(12) United States Patent
Kave (10) Patent No.: US 8,834,485 B2
(45) Date of Patent: Sep. 16, 2014

(54) MEASURING INSTRUMENT FOR SIZING AN ELONGATE STABILIZATION ELEMENT

(75) Inventor: Douglas D Kave, Byhalia, MI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 381 days.

(21) Appl. No.: 12/851,684

(22) Filed: Aug. 6, 2010

(65) Prior Publication Data
US 2012/0035611 A1 Feb. 9, 2012

(51) Int. Cl.
| | |
|---|---|
| A61B 17/58 | (2006.01) |
| A61B 17/60 | (2006.01) |
| A61F 2/00 | (2006.01) |
| A61B 19/00 | (2006.01) |
| A61B 17/70 | (2006.01) |

(52) U.S. Cl.
CPC ......... *A61B 19/46* (2013.01); *A61B 2019/461* (2013.01); *A61B 17/7041* (2013.01); *A61B 17/7074* (2013.01)
USPC .............. 606/102; 606/96; 606/105; 606/205

(58) Field of Classification Search
USPC ................ 606/102, 96–98, 105, 205–209
See application file for complete search history.

(56) References Cited

U.S. PATENT DOCUMENTS

| | | | | |
|---|---|---|---|---|
| 2,181,746 | A * | 11/1939 | Siebrandt | 606/96 |
| 7,618,424 | B2 * | 11/2009 | Wilcox et al. | 606/105 |
| 2004/0158257 | A1 * | 8/2004 | Bonati et al. | 606/99 |
| 2006/0247649 | A1 * | 11/2006 | Rezach et al. | 606/90 |
| 2007/0016296 | A1 * | 1/2007 | Triplett et al. | 623/17.11 |
| 2007/0173745 | A1 | 7/2007 | Diederich | |
| 2008/0234678 | A1 * | 9/2008 | Gutierrez et al. | 606/60 |
| 2008/0255575 | A1 | 10/2008 | Justis et al. | |

* cited by examiner

*Primary Examiner* — Andrew Yang
*Assistant Examiner* — Olivia C Chang
(74) *Attorney, Agent, or Firm* — Sorell Lenna & Schmidt LLP (57) ABSTRACT

A medical instrument includes first and second support members movably coupled to one another to provide variable spacing between distal portions of the support members. A first engagement element is attached to the distal portion of the first support member and extends generally along a first axis, and a second engagement element is attached to the distal portion of the second support member and extends generally along a second axis. At least one of the engagement elements includes an articulating portion articularly engaged with a mounting portion to provide multi-axial movement therebetween to thereby vary an angular orientation of the first axis relative to the second axis. An indicator extends between proximal portions of the support members and includes multiple indicia corresponding to variable distances between the first and second axes adjacent the engagement elements to provide an indication corresponding to a select distance between the first and second axes adjacent the engagement elements.

27 Claims, 7 Drawing Sheets

MEASURING INSTRUMENT FOR SIZING AN ELONGATE STABILIZATION ELEMENT

FIELD OF THE INVENTION

The present invention relates generally to medical instruments, and more particularly relates to a measuring instrument for sizing an elongate stabilization element for positioning along a bony segment.

BACKGROUND

Patients suffering from orthopedic injuries, deformities, or degenerative diseases often require surgery to stabilize an internal structure, promote healing and/or relieve pain. In the spinal field, surgeries to correct spinal abnormalities often involve positioning one or more elongate stabilization elements such as rods, plates or other types of elongate members along a portion of the spinal column, and anchoring each of the elongate stabilization elements to two or more vertebrae via screws, hooks or other types of bone anchors. Prior to anchoring the elongate stabilization element to the spinal column, the surgeon may need to measure the distance between the bone anchors or between two reference locations along the spinal column in order to determine the appropriate length of the elongate stabilization element. In some instances, the bone anchors may be arranged at varying angular orientations, thereby presenting difficulties in accurately measuring the distance between the bone anchors to provide a properly sized elongate stabilization element having a length sufficient for coupling to the bone anchors.

Thus, there is a need for an improved medical instrument that can accurately measure the distance between bone anchors or between two reference locations to determine the appropriate length of an elongate stabilization element to be subsequently coupled to the bone anchors.

SUMMARY

The present invention relates generally to medical instruments, and more particularly relates to a measuring instrument for sizing an elongate stabilization element for positioning along a bony segment.

According to one form, a medical instrument is provided for measuring a spacing between two locations along a bony segment. The instrument includes first and second support members movably coupled to one another to provide variable spacing between distal portions of the support members, a first engagement element attached to the distal portion of the first support member and extending generally along a first axis, and a second engagement element attached to the distal portion of the second support member and extending generally along a second axis. At least one of the engagement elements includes an articulating portion articulately engaged with a mounting portion to provide multi-axial movement therebetween to thereby vary an angular orientation of the first axis relative to the second axis. The instrument further includes an indicator extending between proximal portions of the support members and having multiple indicia corresponding to variable distances between the first and second axes adjacent the engagement elements to provide an indication corresponding to a select distance between the first and second axes adjacent the engagement elements.

According to another form, a medical instrument is provided for measuring a spacing between two locations along a bony segment. The instrument includes first and second support members movably coupled to one another to provide variable spacing between distal portions of the support members, a first articulating member extending generally along a first axis and articularly engaged to a distal portion of the first support member to provide multi-axial movement of the first articulating member to thereby vary an angular orientation of the first axis, and a second articulating member extending generally along a second axis and articularly engaged to a distal portion of the second support member to provide multi-axial movement of the second articulating member to thereby vary an angular orientation of said second axis. The instrument further includes an indicator extending between proximal portions of the support members and having multiple indicia corresponding to variable distances between the first and second axes adjacent the articulating members to provide an indication corresponding to a select distance between the first and second axes adjacent the articulating members.

According to a further form, a system is provided for sizing an elongate stabilization element for positioning along a bony segment. The system includes first and second bone anchors that are each provided with a bone engaging portion adapted for anchoring to bone and a proximal portion adapted for coupling to an elongate stabilization element, and a medical instrument for measuring a spacing between the proximal portions of the bone anchors. The instrument includes a first support member movably coupled to a second support member to provide variable spacing between distal portions of the support members, a first engagement element attached to a distal portion of the first support member and extending generally along a first axis and engaged with the proximal portion of the first bone anchor, and a second engagement element attached to a distal portion of the second support member and extending generally along a second axis and engaged with the proximal portion of the second bone anchor. At least one of the engagement elements includes an articulating portion articularly engaged with a mounting portion to provide multi-axial movement of the articulating portion relative to the mounting portion to thereby vary an angular orientation of the first axis relative to the second axis. The instrument further includes an indicator extending between the proximal portions of the support members and having multiple indicia corresponding to variable distances between the first and second axes adjacent the proximal portions of the bone anchors to provide an indication corresponding to a select distance between the first and second axes adjacent the proximal portions of the bone anchors.

Further embodiments, forms, features, aspects, benefits, objects and advantages of the present invention will become apparent from the detailed description and figures provided herewith.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Figure 1:
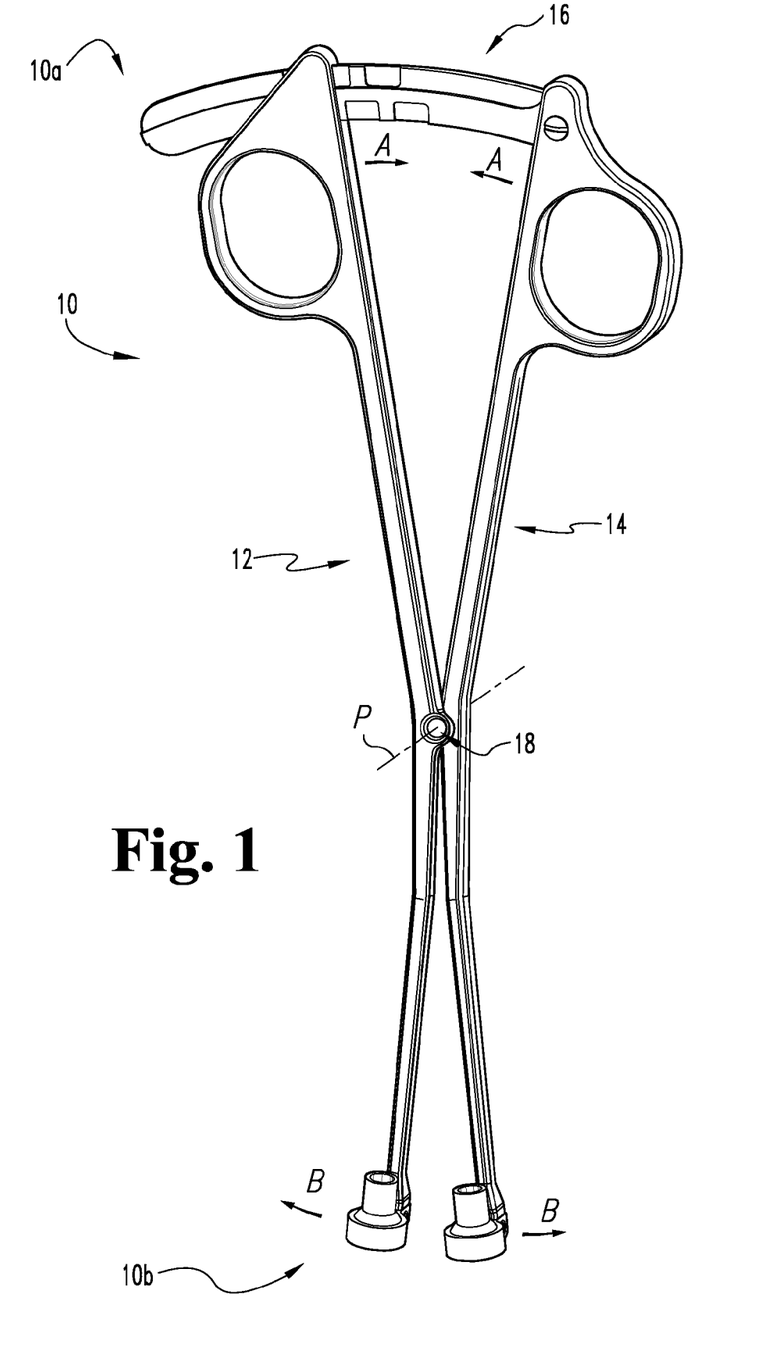
FIG. 1 is a perspective view of a measuring instrument according to one form of the present invention.

Referring to FIG. 1, shown therein is a measuring instrument 10 according to one form of the present invention for sizing an elongate stabilization element for positioning along a bony segment. The measuring instrument 10 has a proximal portion 10a and a distal portion 10b and generally includes first and second elongate support members 12, 14 that are movably coupled to one another, and an indicator or measurement scale 16 that extends between proximal portions of the elongate support members 12, 14 and which is configured to provide an indication or measurement corresponding to the length or spacing between locations along a bony segment, the details of which will be set forth below.

In the illustrated embodiment, the elongate support members 12, 14 are pivotally coupled to one another by way of a pivot member 18 to allow the elongate support members 12, 14 to pivot relative to one another about a pivot axis P such that when the proximal portions of the elongate support members 12, 14 are displaced toward one another in the direction of arrows A, the distal portions of the elongate support members 12, 14 are correspondingly displaced away from one another in the direction of arrows B. However, in an alternative embodiment, the elongate support members 12, 14 may be pivotally coupled to one another such that when the proximal portions of the elongate support members 12, 14 are displaced toward one another, the distal portions of the elongate support members 12, 14 are correspondingly displaced toward one another. In other embodiments, the elongate support members 12, 14 may be movably coupled to one another via other coupling arrangements. For example, in other embodiments, the elongate support members 12, 14 may be movably coupled to one another in a manner which allows for relative linear displacement of the elongate support members 12, 14, or relative displacement of the elongate support members 12, 14 along non-linear or curvi-linear paths. U.S. Patent Application Publication No. 2008/0255575 illustrates and describes a coupling arrangement that may be used in association with the present invention, the contents of which are hereby incorporated by reference in their entirety.

Figure 2:
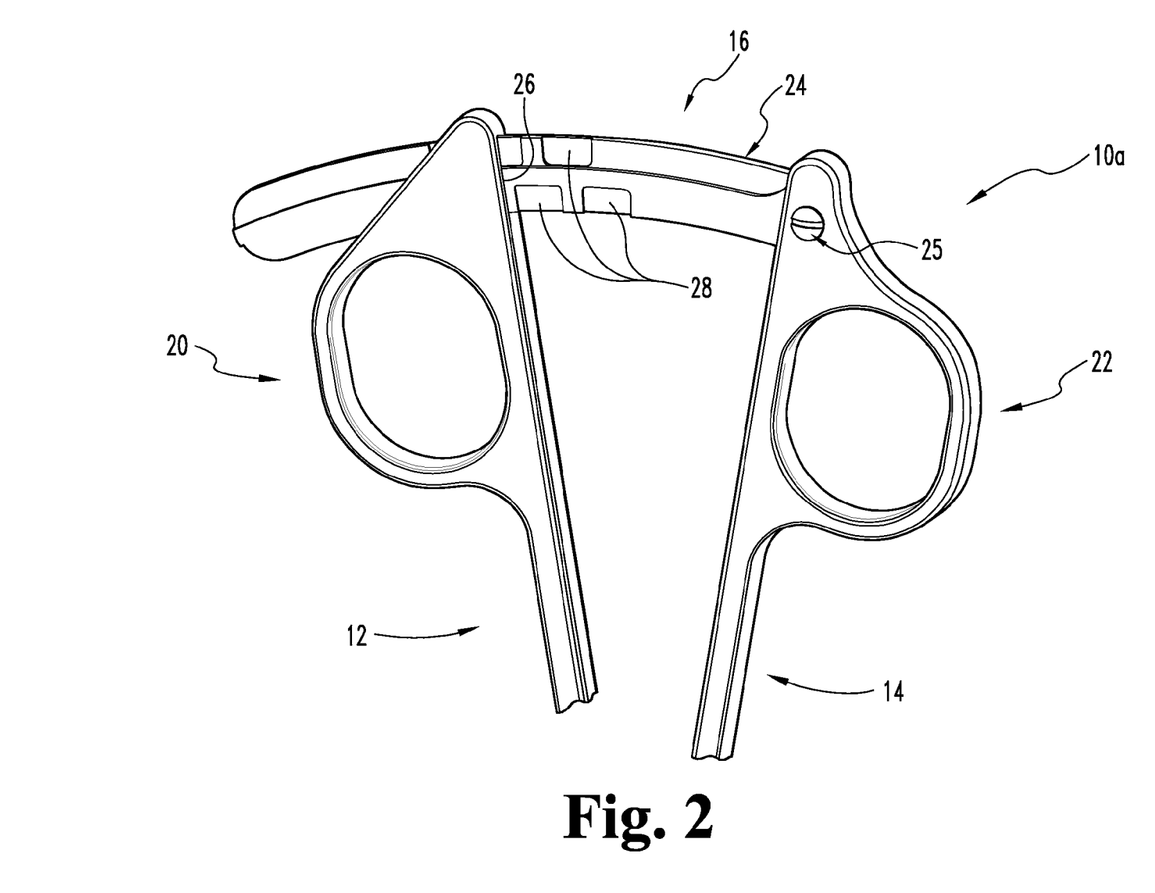
FIG. 2 is a perspective view of the proximal portion of the measuring instrument illustrated in FIG. 1.

Referring to FIG. 2, shown therein is an enlarged perspective view of the proximal portion 10a of the measuring instrument 10. In the illustrated embodiment, the elongate support members 12, 14 each include a proximal handle portion 20, 22, respectively, in the form of a thumb/finger eyelet to facilitate secure grasping and manipulation of the instrument 10 by the user. However, it should be understood that other handle configurations are also contemplated for use in association with the instrument 10. Additionally, it should further be understood that in still other embodiments, the instrument 10 need not necessarily be provided with proximal handle portions.

In the illustrated embodiment, the indicator 16 comprises an elongate plate 24 that is secured in a stationary position relative to the handle portion 22 by way of a fastener 25, and the plate 24 is slidably engaged within a slotted opening 26 formed in the handle portion 22 as the handle portions 20, 22 are moved toward and away from one another. The elongate plate 24 includes a series of indicia 28 or a measurement scale positioned along a length of the plate 24. In one embodiment, the series of indicia 28 correspond to variable distances between first and second axes defined by bone anchor engagement elements that are attached to distal portions of the support members 10, 12 to provide an indication or measurement corresponding to a select distance or spacing between locations along a bony segment. The indicia 28 can take many forms that correspond to the distance or spacing between locations along a bony segment including, for example, markings, numerals, letters, symbols, scaled lines, varying colors, raised surface regions, recessed surface regions, or other forms of indicia that would be apparent to those having ordinary skill in the art. In the illustrated embodiment, the reference location or pointer that is alignable with the individual indicia or marking which corresponds to a select distance or spacing between the locations along the bony segment is the inner edge of the handle portion 20. However, other types of reference locations or pointers are also contemplated including, for example, a window or opening in the handle portion 20 which reveals the particular indicia or marking which corresponds to the select distance or spacing between the locations along the bony segment.

Figure 3:
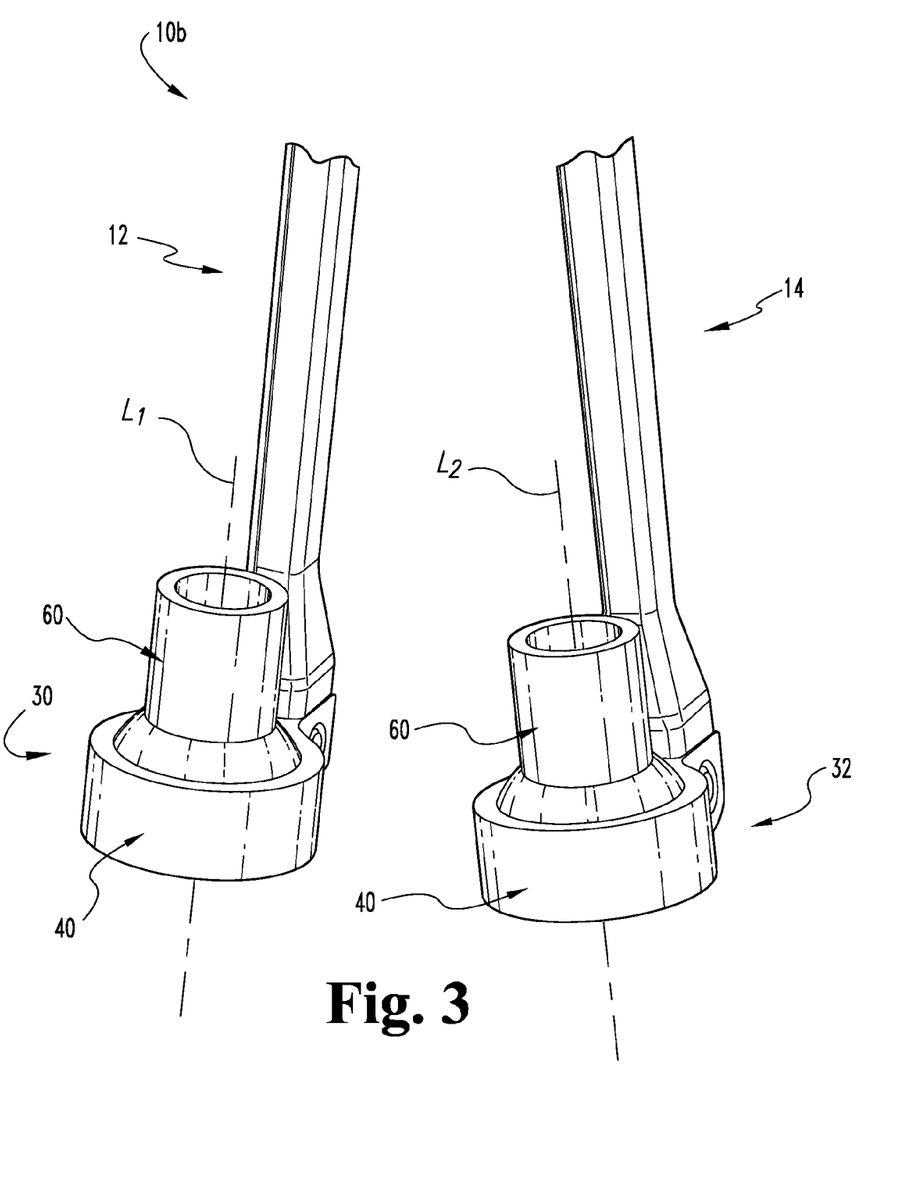
FIG. 3 is a perspective view of the distal portion of the measuring instrument illustrated in FIG. 1.

Referring to FIG. 3, shown therein is an enlarged perspective view of the distal portion 10b of the measuring instrument 10. In the illustrated embodiment, anchor engagement elements 30, 32 are operably attached to the distal portions of the elongate support members 12, 14, respectively. In one embodiment, the anchor engagement elements 30, 32 are configured substantially identical to one another. However, as discussed below, in other embodiments the anchor engagement elements 30, 32 may be provided with different configurations. In the illustrated embodiment of the measuring instrument 10, each of the anchor engagement elements 30, 32 includes a mounting portion 40 and an articulating portion 60, with the articulating portion 60 of the anchor engagement element 30 extending generally along a longitudinal axis $L_1$ and the articulating portion 60 of the anchor engagement element 32 extending generally along a longitudinal axis $L_2$. The articulating portions 60 are articularly engaged to the mounting portions 40 to allow variable multi-axial movement of the articulating portions 60 relative to the mounting portions 40 to thereby vary an angular orientation of the longitudinal axis $L_1$ relative to the longitudinal axis $L_2$, the details of which will be discussed below. In the illustrated embodiment, each of the anchor engagement elements 30, 32 includes an articulating portion 60 that is articularly engaged to a mounting portion 40. However, it should be understood that in an alternative embodiment, only one of the anchor engagement elements 30, 32 need be provided with an articulating portion 60, with the other anchor engagement element including a non-articulating portion that is rigidly and non-movably mounted to the distal end portion of the corresponding support member 12, 14. As should be appreciated, in this alternative embodiment including a single articulating portion 60, the measuring instrument would still permit varying angular orientations of the longitudinal axis $L_1$ relative to the longitudinal axis $L_2$ axis.

Figure 4:
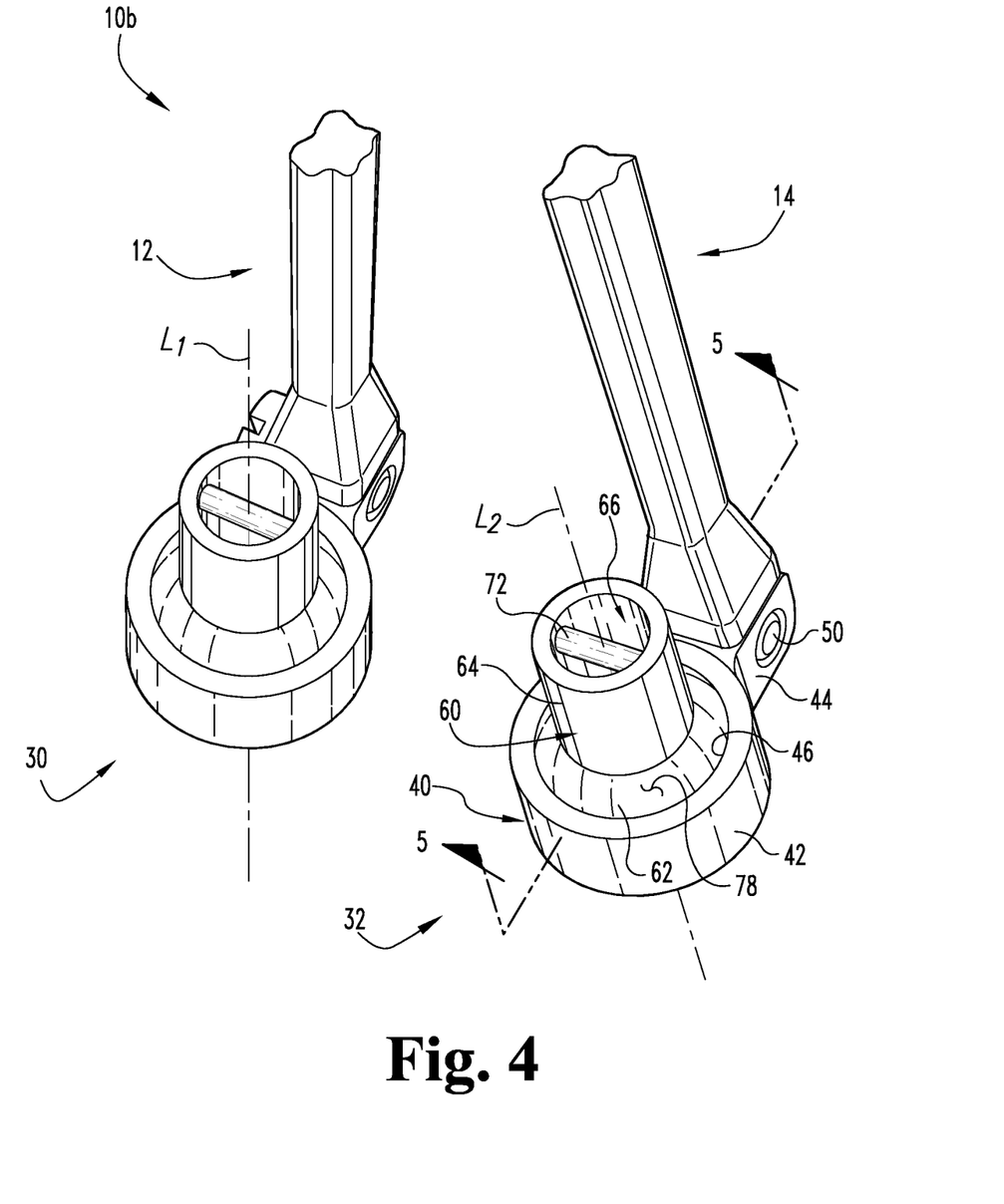
FIG. 4 is another perspective view of the distal portion of the measuring instrument illustrated in FIG. 1.
Figure 5:
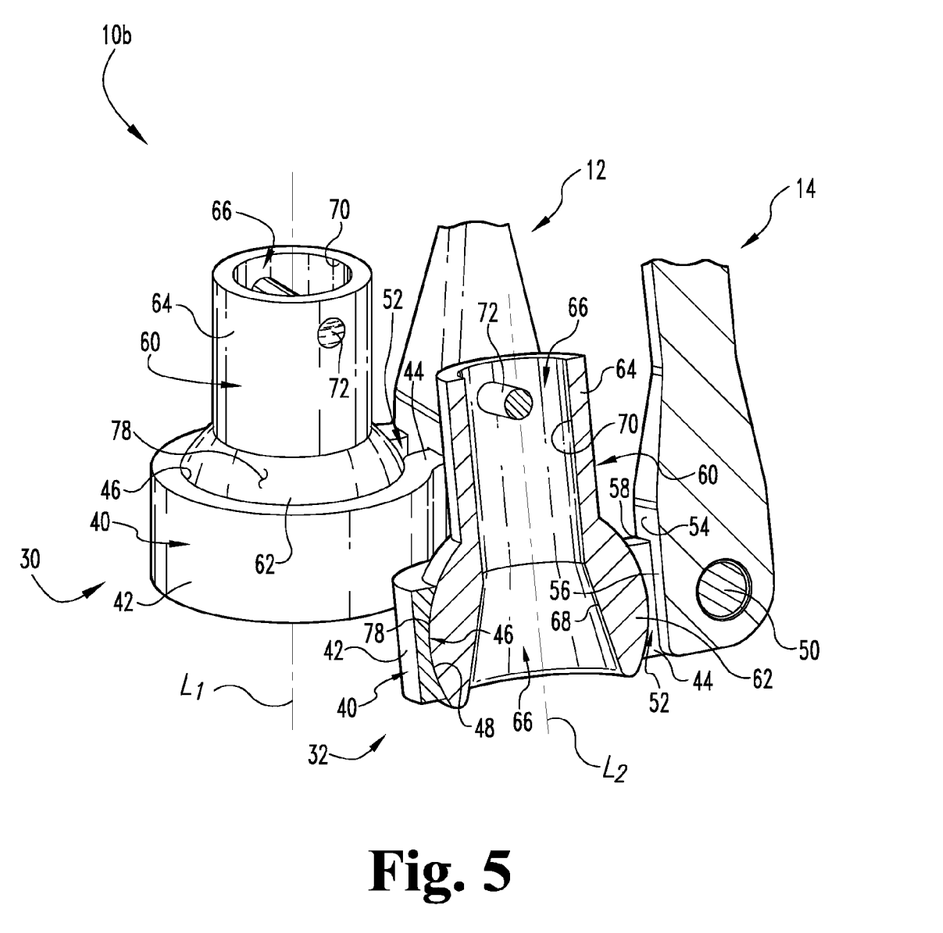
FIG. 5 is a partial cross-sectional perspective view of the distal portion of the measuring instrument of FIG. 4, as taken along line 5-5 of FIG. 4.

Referring now to FIGS. 4 and 5, shown therein are further details regarding the anchor engagement elements 30, 32 associated with the elongate support members 12, 14, respectively. In the illustrated embodiment, the mounting portion 40 includes an annular ring-shaped portion 42 and a flanged portion 44 extending laterally from the ring-shaped portion 42. The annular ring-shaped portion 42 defines a socket 46 sized for receipt of a corresponding portion of the articulating portion 60 to permit multi-axial movement of the articulation portion 60 relative to the mounting portion 40. In one embodiment, the annular portion 42 includes an inner surface 48 having a spherical shape to provide the socket 46 with an at least partially spherical configuration. However, other means for articularly connecting the articulating portion 60 to the mounting portion 40 to provide multi-axial movement therebetween are also contemplated as would occur to those having ordinary skill in the art. For example, in another embodiment, the mounting portion may be configured to include a spherical-shaped ball that is received within a spherical-shaped socket defined by the articulating portion 60. Additionally, in yet another embodiment, the articulating portion 60 may be connected to the mounting portion 40 via a flexible connection element to permit multi-axial movement of the articulation portion 60 relative to the mounting portion 40. The flanged portion 44 is engaged to and extends transversely from the distal region of the respective elongate member 12, 14 via a pin or fastener 50. However, in other embodiments, the flanged portion 44 may be engaged to the distal region of the respective elongate members 12, 14 via other means of attachment, or the flanged portion 44 may be formed integrally with the respective elongate member 12, 14 to provide a unitary, single-piece structure.

In the illustrated embodiment, the mounting portion 40 is stationarily engaged to the distal end portion of the respective elongate member 12, 14. However, other embodiments are also contemplated where the mounting portion 40 may be movably engaged to the distal end portion of the respective elongate member 12, 14 to provide translational, rotational and/or pivotal movement therebetween. Additionally, in one embodiment, the mounting portion 40 includes a slot 52 extending from the lateral end of the flanged portion 44 and into the socket 46 of the ring-shaped portion 42 to provide a degree of flexibility to the mounting portion 40 such that the ring-shaped portion 42 may be expanded to allow positioning of the articulating portion 60 within the socket 46, and thereafter contracted about the articulating portion 60 to capture and retain the articulating portion 60 within the socket 46. Additionally, in one embodiment, the distal regions of the elongate support members 12, 14 may be provided with a base portion 54 and a projecting portion 56 extending from the base portion 54 and having a somewhat narrower width relative to the base portion 54 so as to define a pair of shoulders 58 against which edges of the flanged portion 44 are engaged to prevent rotation of the mounting portion 40 relative to the elongate elements 12, 14. Although a specific configuration of the mounting portion 40 is illustrated and described herein, it should be understood that other configurations of the mounting portion 40 are also contemplated as falling with the scope of the present invention.

In the illustrated embodiment, the articulating portion 60 includes a ball portion 62, a stem portion 64 extending axially from the ball portion 62, and an axial passage 66 extending generally along the longitudinal axis $L_1$, $L_2$ and through the ball portion 62 and at least partially into the stem portion 64. A distal region of the axial passage 66 adjacent the ball portion 62 includes a conical inner surface 68 that tapers inwardly from the distal end of the ball portion 62 toward the stem portion 64. A proximal region of the axial passage 66 includes a cylindrical inner surface 70 extending proximally from the conical inner surface 68. The articulating portion 60 further includes a stop element 72 extending at least partially into the axial passage 66, the purpose of which will be set forth below. In the illustrated embodiment, the stop element 72 comprises a rod or bar extending across at least a portion of the passage 66. However, other configurations of stop elements are also contemplated including, for example, providing a wall extending across a proximal region of the axial passage 66 or providing the inner surface of the stem portion 64 with an annular shoulder extending into the axial passage 66.

As shown most clearly in FIG. 5, in the illustrated embodiment, the ball portion 62 of the articulating portion 60 includes an outer surface 78 having a spherical configuration to provide the ball portion 62 with an at least partially spherical shape which corresponds to the spherical shape of the inner surface 48 defined by the socket 46 in the mounting portion 40. As should be appreciated, the spherical-shaped ball portion 62 is articularly engaged within the spherical-shaped socket 46 to provide a swivel-type connection that permits variable multi-axial movement of the articulating portion 60 relative to the mounting portion 40. In other word, the ball portion 62 is permitted to rotate/pivot within the socket 46 in all directions to variably position the longitudinal axis $L_1$, $L_2$ of the articulating portion 60 along multiple planes or axes to accommodate for varying bone anchor orientations, the details of which will be set forth below. However, in other embodiments, the articulating portions 60 of the engagement elements 30, 32 may be configured to provide at least two degrees of freedom or articular movement between the engagement elements 30, 32 in at least two directions to variably position the longitudinal axis $L_1$, $L_2$ along at least two planes or axes to accommodate for varying bone anchor orientations.

Figure 6:
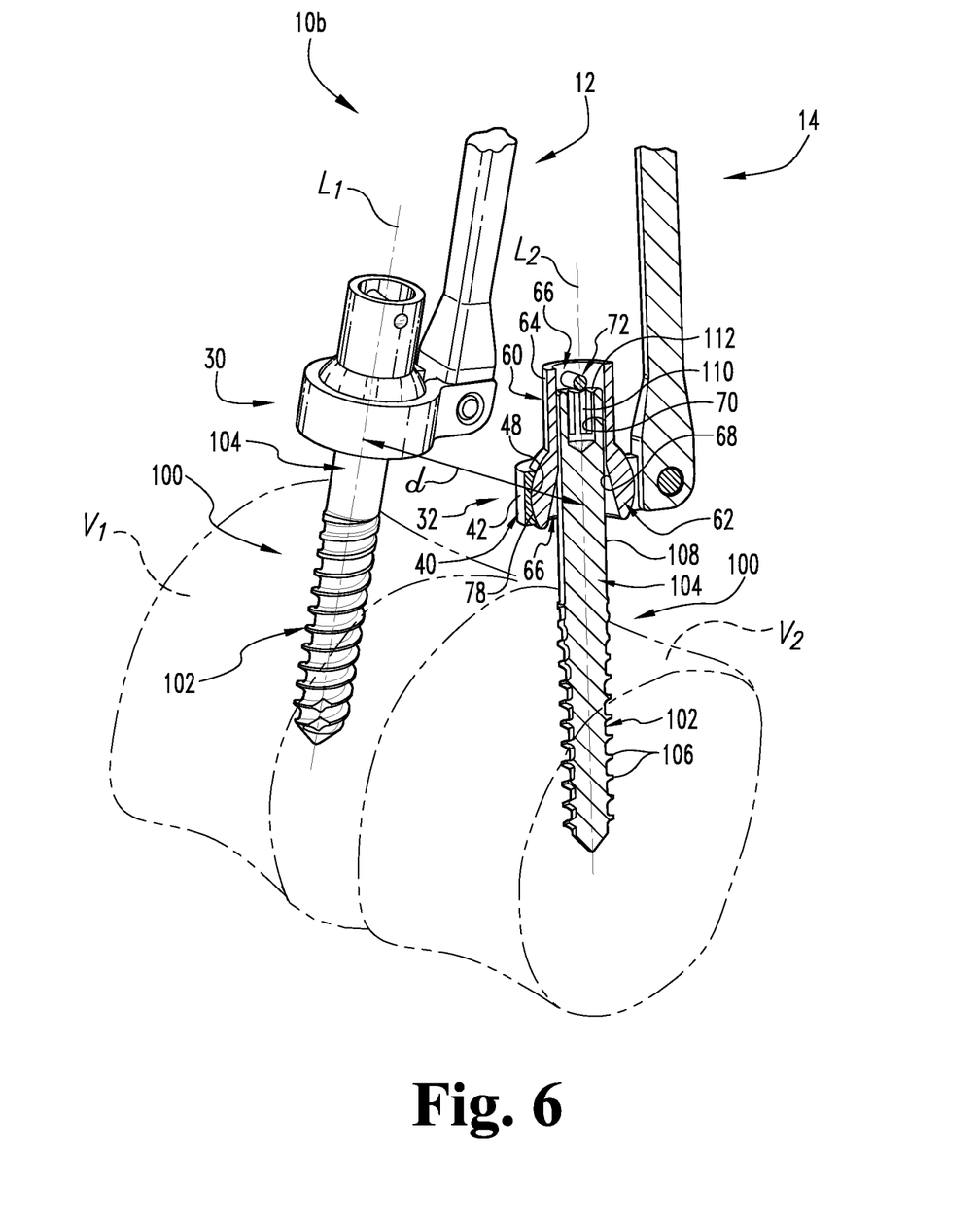
FIG. 6 is a partial cross-sectional perspective view of the distal portion of the measuring instrument illustrated in FIG. 1, as engaged with a pair of bone anchors anchored to respective vertebrae.

Referring to FIG. 6, shown therein are a pair of bone anchors 100 anchored to respective vertebrae $V_1$, $V_2$ which can comprise all or a portion of the cervical, thoracic, lumbar and sacral vertebrae of the spinal column. In one embodiment, the bone anchors 100 are engaged to the pedicle regions of the vertebrae $V_1$, $V_2$. However, it should be understood that the bone anchors 100 may be engaged to any number of vertebrae and/or to other portions or regions of the vertebrae. Each of the bone anchors 100 extends along a longitudinal axis and generally includes a distal bone engaging portion 102 adapted for anchoring to bone, and a proximal portion 104 configured for coupling to an elongate stabilization element 120 (FIG. 7), the details of which will be set forth below.

In the illustrated embodiment, the bone anchors 100 are each configured as a bone screw, with the bone engaging portion 102 comprising a threaded shank including external threads 106 configured for anchoring in bone. Although the illustrated embodiment of bone anchor 100 is configured as a bone screw including a threaded shank, it should be understood that the bone engaging portion 102 may alternatively be provided with other bone engaging structures such as, for example, barbs, ratchets, spikes, pivoting gulls or other types of projections configured to engage bony tissue. In still other embodiments, the bone engaging portion 102 may be provided in the form of a bolt, a pin, a hook configured to engage and wrap about a portion of a vertebral body, a staple, an interbody device, an intrabody device, or any other suitable bone engaging structure that would occur to those having ordinary skill in the art.

Additionally, in the illustrated embodiment, the proximal portion 104 of the bone anchor 100 comprises a non-threaded stem or post portion having a length extending generally along the longitudinal axis of the bone anchor and defining a circular cylindrical outer surface 108. The proximal portion 104 also defines a hexagonal-shaped tool engaging recess 110 extending from the proximal end 112 in a distal direction and configured to receive a distal end portion of a driving tool (not shown) to facilitate threading engagement of the threaded shank 102 into bone. However, other types of bone anchors are also contemplated, including bone anchors having proximal portions defining a channel or passage for receiving an elongate support member. For example, bone anchors including a proximal head portion having a U-shaped, a C-shaped, or an enclosed channel or passage configured to receive an elongate support member or spinal rod are also contemplated for use in association with the present invention. Additionally, although the bone anchor 100 has been illustrated and described as having a unitary, single-piece configuration, it should be understood that other types of bone anchors having multi-piece configurations are also contemplated as falling within the scope of the present invention. For example, in other embodiments, the bone anchors may be configured to include a proximal head portion that is movably engaged to the bone engaging portion such, for example, a multi-axial bone screw.

Having discussed the elements and features associated with the measuring instrument 10, a procedure for using the measuring instrument 10 to measure a spacing between two locations along a bony segment to size an elongate stabilization element for positioning along the bony segment will now be discussed. However, it should be understood that the disclosed procedure is exemplary and is not intended to limit the scope of the present invention.

As illustrated in FIG. 6, the bone anchors 100 are anchored to the respective vertebrae $V_1, V_2$ via engagement of the distal bone engaging portions 102 in vertebral bone, with the proximal portions 104 of the bone anchors 100 extending outwardly from the vertebrae $V_1, V_2$. As indicated above, the longitudinal axes of the proximal anchor portions 104 may not necessarily be arranged parallel to one another, and may be misaligned in more than one dimension (i.e., the longitudinal axes of the bone anchors 100 may be positioned along different planes). The measuring instrument 10 may be used to accommodate for non-parallel and/or misaligned orientations of the proximal anchor portions 104 to provide an accurate measurement of the spacing or distance therebetween.

As indicated above, the support members 12, 14 are movably coupled (i.e., pivotally connected) to one another to provide variable spacing between the engagement elements 30, 32 that are attached to the distal portions of the support members 12, 14, respectively. The spacing between the engagement elements 30, 32 may be adjusted via manipulation of the handle portions 20, 22 by the user to generally align the engagement elements 30, 32 with the proximal portions 104 of the bone anchors 100. The engagement elements 30, 32 are then engaged with the proximal anchor portions 104 via insertion of the proximal anchor portions 104 into the axial passages 66 of the articulating portions 60. As indicated above, insertion of the proximal anchor portions 104 into the passages 66 is facilitated by the conical inner surface 68 formed along the distal region of each passage 66 which serves to guide the proximal anchor portion 104 into the cylindrical proximal region of the passage 66. The proximal anchor portions 104 are inserted into the passages 66 to a prescribed depth that is dictated by abutment of the distal ends 112 of the bone anchors 100 against the stop element 72.

In the illustrated embodiment, the proximal anchor portion 104 has a circular outer cross section that is sized in relatively close tolerance with the circular inner cross section of the proximal cylindrical region of the passage 66 to provide a relatively close fitting arrangement therebetween to substantially align the longitudinal axes $L_1, L_2$ of the articulating portions 60 with the longitudinal axes of the corresponding bone anchors 100. In order to accommodate for possible non-parallel and/or misaligned orientations of the proximal anchor portions 104, the articulating portions 60 are permitted to rotate/pivot relative to the mounting portions 40 to provide multi-axial movement of the articulating portion 60 via the swivel connection provided by the ball- and socket arrangement defined between the articulating portions 60 and the mounting portions 40. The multi-axial movement of the articulating portion 60 in turn varies the relative angular orientation of the longitudinal axes $L_1, L_2$ to substantially align the longitudinal axes $L_1, L_2$ of the articulating portions 60 with the longitudinal axes of the proximal anchor portions 104.

Although the illustrated embodiment of the measuring instrument 10 provides engagement of the distal portions of the support members 12, 14 with the proximal portions 104 of the bone anchors 100 via insertion of the proximal anchor portions 104 into the passages 66 formed in the articulating portions 60, it should be understood that other embodiments for engaging the measuring instrument 10 with the bone anchors 100 are also contemplated. For example, in one alternative embodiment, the articulating portions 60 may be provided with protrusions or stems that are positionable in apertures formed in the proximal portions of the bone anchors (i.e., in the tool receiving recesses 110 formed in the proximal anchor portions 104) to substantially align the longitudinal axes of the engagement elements with the proximal anchor portions. Other means for engaging the distal portions of the support members 10, 12 with the proximal anchor portions 104 are also contemplated as would occur to those having ordinary skill in the art.

Once the engagement elements 30, 32 are properly engaged with the proximal portions 104 of the bone anchors 100 (as shown in FIG. 6), the indicator 16 provides an indication to the user which corresponds to the select distance d between the longitudinal axes $L_1, L_2$ at a point adjacent the location where the engagement elements 30, 32 engage the proximal anchor portions 104. As shown in FIG. 2, in the illustrated embodiment, the reference location or pointer that is alignable with the individual indicia or marking which corresponds to the select distance d is the inner edge of the handle portion 20. However, as indicated above, other reference locations or pointers are also contemplated which provide an indication that corresponds to the select distance d.

Figure 7:
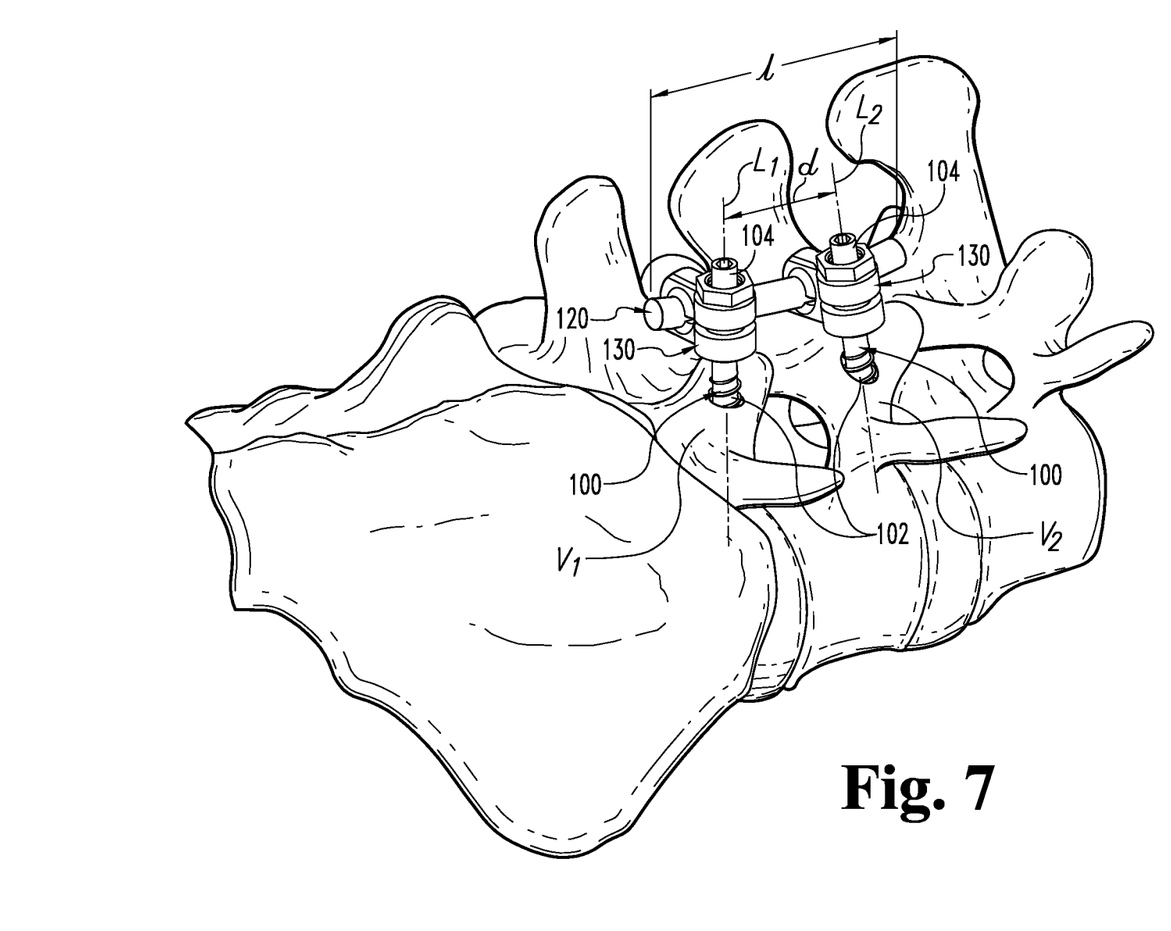
FIG. 7 is a perspective view of a portion of the spinal column including a pair of bone anchors anchored to respective vertebrae and an elongate stabilization element coupled to the bone anchors.

Referring to FIG. 7, once the select distance d between the longitudinal axes $L_1, L_2$ is determined via the measuring instrument 10, an elongate stabilization element 120 having an appropriate length l sufficient to span the distance between the proximal portions 104 of the bone anchors 100 is selected based on the indication or measurement provided by the measuring instrument 10. The elongate stabilization element 120 having the length/is thereafter coupled to the proximal portions 104 of the bone anchors 100. In the illustrated embodiment, the elongate stabilization element 120 is configured as a spinal rod having a circular outer cross section. However, it should be understood that other types and configurations of elongate stabilization elements and other cross-sectional shapes and configurations of spinal rods are also contemplated as falling within the scope of the present invention. Additionally, in the illustrated embodiment, the elongate stabilization element 120 is coupled to the proximal portions 104 of the bone anchors 100 via a connector or coupling device 130. One embodiment of a connector suitable for use in association with the present invention is illustrated and described in U.S. Pat. No. 6,626,906, the contents of which are incorporated herein by reference in their entirety. However, it should be understood that other types and configurations of connectors or coupling devices are also contemplated as falling with the scope of the present invention.

While the invention has been illustrated and described in detail in the drawings and foregoing description, the same is to be considered as illustrative and not restrictive in character, it being understood that only the preferred embodiments have been shown and described and that all changes and modifications that fall within the spirit of the invention are desired to be protected. Any theory, mechanism of operation, proof or finding stated herein is meant to further enhance understanding of the present invention, and is not intended to make the present invention in any way dependent upon such theory, mechanism of operation, proof or finding. It should be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

What is claimed is:

1. A medical instrument for measuring a spacing between two locations along a bony segment, comprising:
    first and second support members each including a proximal portion and a distal portion, said first support member movably coupled to said second support member to provide variable spacing between said distal portions of said support members;
    a first engagement element attached to said distal portion of said first support member and extending generally along a first axis, a second engagement element attached to said distal portion of said second support member and extending generally along a second axis, at least one of said engagement elements including an articulating portion articularly engaged with a mounting portion to provide multi-axial movement of said articulating portion relative to said mounting portion to thereby vary an angular orientation of said first axis relative to said second axis, said articulating portion defining an axial passage including a transverse stop member extending across a core of said axial passage, said articulating portion and said mounting portion being engaged to one another by a ball and socket connection arrangement to provide said multi-axial movement of said articulating portion relative to said mounting portion; and
    an indicator extending between proximal portions of said first and second support members, said indicator including multiple indicia corresponding to variable distances between said first and second axes of said engagement elements adjacent said engagement elements to provide an indication corresponding to a select distance between said first and second axes adjacent said engagement elements.

2. The instrument of claim 1, wherein said stop member completely blocks extends completely across said axial passage and said first and second support members are pivotally coupled to one another to allow pivotal movement about a pivot axis to provide said variable spacing between said distal portions of said support members.

3. The instrument of claim 2, wherein said proximal portions of said first and second support members comprise handle portions; and
    wherein pivotal movement of said handle portions relative to said pivot axis provides said variable spacing between said distal portions of said support members.

4. The instrument of claim 1, wherein said indicator comprises a scale member attached to said proximal portion of one of said support members and movably engaged with said proximal portion of the other of said support members.

5. The instrument of claim 1, wherein said indicator comprises a scale member and said indicia comprise markings positioned along a length of said scale member, one of said markings alignable with a pointer associated with one of said support members to provide said indication corresponding to said select distance between said first and second axes adjacent said engagement elements.

6. The instrument of claim 1, wherein each of said first and second engagement elements includes said articulating portion articularly engaged with said mounting portion to provide said multi-axial movement of said articulating portion relative to said mounting portion.

7. The instrument of claim 1, wherein said multi-axial movement comprises at least two degrees of articular movement between said articulating portion and said mounting portion.

8. The instrument of claim 1, wherein said articulating portion pivots relative to said mounting portion in all directions.

9. The instrument of claim 1, wherein said articulating portion and said mounting portion are engaged to one another by a swivel connection arrangement to provide said multi-axial movement of said articulating portion relative to said mounting portion.

10. The instrument of claim 1, wherein said mounting portion defines a socket and said articulating portion defines a ball articularly engaged within said socket to provide said ball and socket connection arrangement.

11. The instrument of claim 1, wherein said ball and socket connection arrangement comprises a ball defining a spherical-shaped outer surface and a socket defining a spherical-shaped inner surface, said spherical-shaped outer surface articularly engaged with said spherical-shaped inner surface to provide said multi-axial movement of said articulating portion relative to said mounting portion.

12. The instrument of claim 1, wherein said axial passage is generally aligned along a corresponding one of said first and second axes, said axial passage sized to receive a proximal portion of a bone anchor therein to thereby align said proximal portion of said bone anchor generally along said corresponding one of said first and second axes.

13. The instrument of claim 12, wherein a portion of said axial passage defines an inner cross section corresponding to an outer cross section of said proximal portion of said bone anchor, said inner cross section engaged with said outer cross section in a relatively close fitting arrangement to thereby align said proximal portion of said bone anchor generally along said corresponding one of said first and second axes.

14. The instrument of claim 13, wherein said inner and outer cross sections are each circular.

15. The instrument of claim 12, wherein said axial passage is bound by an inner surface, a distal region of said inner surface tapering inwardly from a location adjacent a distal end of said articulating portion toward a proximal end of said articulating portion to facilitate positioning of said proximal portion of said bone anchor within said axial passage.

16. The instrument of claim 15, wherein said distal region of said inner surface has a conical shape.

17. The instrument of claim 12, wherein said transverse stop member locates said proximal portion of said bone anchor at a prescribed axial position when said proximal portion of said bone anchor is positioned in abutment against said stop member.

18. The instrument of claim 1, further comprising first and second bone anchors each including a bone engaging portion adapted for anchoring to bone and a proximal portion adapted for coupling to an elongate stabilization element; and
wherein said first engagement element is engaged with said proximal portion of said first bone anchor; and
wherein said second engagement element is engaged with said proximal portion of said second bone anchor.

19. A medical instrument for measuring a spacing between two locations along a bony segment, comprising:
first and second support members each including a proximal portion and a distal portion, said first support member movably coupled to said second support member to provide variable spacing between said distal portions of said support members;
a first articulating member extending generally along a first axis and articularly engaged to said distal portion of said first support member to provide multi-axial movement of said first articulating member relative to said first support member to thereby vary an angular orientation of said first axis, said first articulating member defining a first axial passage including a transverse stop member extending across a core of said first axial passage;
a second articulating member extending generally along a second axis and articularly engaged to said distal portion of said second support member to provide multi-axial movement of said second articulating member relative to said second support member to thereby vary an angular orientation of said second axis, said second articulating member defining a second axial passage including a transverse stop member extending across a core of said second axial passage, wherein said first and second articulating members are respectively engaged to said distal portions of said first and second support members by a ball and socket connection arrangement to provide said multi-axial movement; and
an indicator extending between proximal portions of said first and second support members, said indicator including multiple indicia corresponding to variable distances between said first and second axes adjacent said articulating members to provide an indication corresponding to a select distance between said first and second axes adjacent said articulating members.

20. The instrument of claim 19, wherein said first and second articulating members are respectively engaged to said distal portions of said first and second support members by a swivel connection arrangement to provide said multi-axial movement.

21. The instrument of claim 19, wherein said ball and socket connection arrangement comprises a ball defining a spherical-shaped outer surface and a socket defining a spherical-shaped inner surface, said spherical-shaped outer surface articularly engaged with said spherical-shaped inner surface to provide said multi-axial movement.

22. The instrument of claim 19, wherein axial passage is generally aligned along a corresponding one of said first and second axes, said axial passage sized to receive a proximal portion of a bone anchor therein to align said proximal portion of said bone anchor generally along said corresponding one of said first and second axes.

23. A system for sizing an elongate stabilization element for positioning along a bony segment, comprising:
first and second bone anchors each including a bone engaging portion adapted for anchoring to bone and a proximal portion adapted for coupling to an elongate stabilization element;
a medical instrument for measuring a spacing between said proximal portions of said first and second bone anchors, said medical instrument including:
first and second support members each including a proximal portion and a distal portion, said first support member movably coupled to said second support member to provide variable spacing between said distal portions of said support members;
a first engagement element attached to said distal portion of said first support member and extending generally along a first axis, said first engagement element engaged with said proximal portion of said first bone anchor;
a second engagement element attached to said distal portion of said second support member and extending generally along a second axis, said second engagement element engaged with said proximal portion of said second bone anchor;
at least one of said engagement elements including an articulating portion articularly engaged with a mounting portion to provide multi-axial movement of said articulating portion relative to said mounting portion to thereby vary an angular orientation of said first axis relative to said second axis, said articulating portion defining an axial passage including a transverse member extending across a center core of said axial passage, wherein said articulating portion and said mounting portion are engaged to one another by a ball and socket connection arrangement to provide said multi-axial movement of said articulating portion relative to said mounting portion; and
an indicator extending between proximal portions of said first and second support members, said indicator including multiple indicia corresponding to variable distances between said first and second axes adjacent said proximal portions of said bone anchors to provide an indication corresponding to a select distance between said first and second axes adjacent said proximal portions of said bone anchors.

24. The system of claim 23, wherein each of said first and second engagement elements includes said articulating portion articularly engaged with said mounting portion to provide said multi-axial movement of said articulating portion relative to said mounting portion.

25. The system of claim 23, wherein said articulating portion and said mounting portion are engaged to one another by a swivel connection arrangement to provide said multi-axial movement of said articulating portion relative to said mounting portion.

26. The system of claim 23, wherein said ball and socket connection arrangement comprises a ball defining a spherical-shaped outer surface and a socket defining a spherical-shaped inner surface, said spherical-shaped outer surface engaged with said spherical-shaped inner surface to provide said multi-axial movement of said articulating portion relative to said mounting portion.

27. The system of claim 23, wherein said first and second bone anchors each comprise a bone screw, wherein said bone engaging portion comprises a threaded shank, and wherein said proximal portion comprises a cylindrical shaped post extending axially from said threaded shank.

* * * * *